US010996333B2

(12) United States Patent
Van Rens et al.

(10) Patent No.: US 10,996,333 B2
(45) Date of Patent: May 4, 2021

(54) ULTRASOUND SYSTEM FOR PROVIDING ULTRASOUND IMAGES AT VARIABLE FREQUENCIES OF A VOLUMETRIC REGION COMPRISING AN INTERFERER ANALYZER

(71) Applicant: KONINKLIJKE PHILIPS N.V., Eindhoven (NL)

(72) Inventors: Antonia Cornelia (Jeannet) Van Rens, Eindhoven (NL); Wendy Uyen Dittmer, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 437 days.

(21) Appl. No.: 15/769,090

(22) PCT Filed: Oct. 28, 2016

(86) PCT No.: PCT/EP2016/076008
§ 371 (c)(1),
(2) Date: Apr. 18, 2018

(87) PCT Pub. No.: WO2017/076758
PCT Pub. Date: May 11, 2017

(65) Prior Publication Data
US 2018/0306919 A1    Oct. 25, 2018

(30) Foreign Application Priority Data
Nov. 2, 2015    (EP) ..................................... 15192490

(51) Int. Cl.
*G01S 15/89*    (2006.01)
*G01S 7/52*    (2006.01)
(Continued)

(52) U.S. Cl.
CPC ............ *G01S 15/8952* (2013.01); *A61B 8/00* (2013.01); *A61B 8/52* (2013.01); *G01S 7/52046* (2013.01);
(Continued)

(58) Field of Classification Search
CPC ............ G01S 15/8592; G01S 7/52406; G01S 7/52407; G01S 7/52063; G01S 7/52073;
(Continued)

(56) References Cited

U.S. PATENT DOCUMENTS

| 4,631,710 A | 12/1986 | Yamaguchi et al. |
| 5,549,111 A * | 8/1996 | Wright ................ G01S 15/895 600/443 |

(Continued)

FOREIGN PATENT DOCUMENTS

| EP | 2290394 A2 | 3/2011 |
| WO | 2015028314 A1 | 3/2015 |
| WO | 2015028949 A1 | 3/2015 |
| WO | 2015086413 A1 | 6/2015 |

OTHER PUBLICATIONS

Ponnle et al "Suppression of Grating Lobe Artifacts in Ultrasound Images" Ultrasound in Med. & Biol. vol. 39, No. 4 (2013) p. 681-691.
(Continued)

*Primary Examiner* — Rochelle D Turchen
*Assistant Examiner* — Chao Sheng

(57) ABSTRACT

An ultrasound system (100) for providing an ultrasound image of a volumetric region comprising a region of interest (12) comprising: a probe (10) having an array of CMUT transducers (14); a beamformer (64) coupled to the array and adapted to control the ultrasound beam steering and provide an ultrasound image data of the volumetric region; a transducer frequency controller (62) coupled to the beamformer and adapted to vary operation frequencies of the CMUT
(Continued)

transducers within the frequency range, which frequency controller is arranged to set the operation frequency to a first frequency for the ultrasound beam steered in the volumetric region and to set the operation frequency to a second frequency for the ultrasound beams steered within the region of interest, the second frequency being higher than the first frequency; wherein the system further comprises an interferer analyzer (69) coupled to the transducer frequency controller (62), said interferer analyzer is adapted to vary at least one of beam steering parameters when the second frequency is above a threshold frequency value so as to mitigate a quality reduction of the ultrasound image due to the use of frequencies above the threshold.

14 Claims, 10 Drawing Sheets

(51) Int. Cl.
  *G10K 11/34* (2006.01)
  *A61B 8/00* (2006.01)
  *A61B 8/08* (2006.01)

(52) U.S. Cl.
  CPC ...... *G01S 7/52063* (2013.01); *G01S 7/52073* (2013.01); *G01S 7/52074* (2013.01); *G01S 15/8993* (2013.01); *G10K 11/343* (2013.01); *G01S 7/52047* (2013.01)

(58) Field of Classification Search
  CPC ............ G01S 7/52074; G01S 15/8993; G10K 11/343; A61B 8/00; A61B 8/52
  See application file for complete search history.

(56) References Cited

U.S. PATENT DOCUMENTS

| | | | |
|---|---|---|---|
| 5,873,830 A | 2/1999 | Hossack et al. | |
| 6,328,697 B1 | 12/2001 | Fraser | |
| 7,529,393 B2 | 5/2009 | Peszynski et al. | |
| 2003/0149363 A1* | 8/2003 | Dreschel | A61B 8/4483 600/437 |
| 2005/0033165 A1* | 2/2005 | Ustuner | G01S 7/52047 600/437 |
| 2007/0236492 A1* | 10/2007 | Ahn | G01S 7/52033 345/418 |
| 2011/0040179 A1* | 2/2011 | Shin | G01S 7/52047 600/437 |

OTHER PUBLICATIONS

Yeh et al "3D Ultrasound Imaging Using a Forward Looking CMUT Ring Array for Intravascular/Intracardiac Applications" IEEE Transactions on Ultrasonics, Ferroelectrics and Frequency Control., vol. 53, No. 6, Jun. 1, 2006, p. 1202-1211.

* cited by examiner

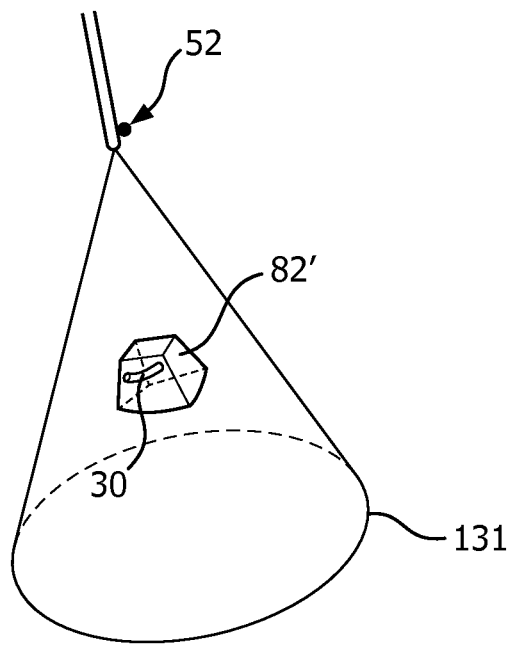
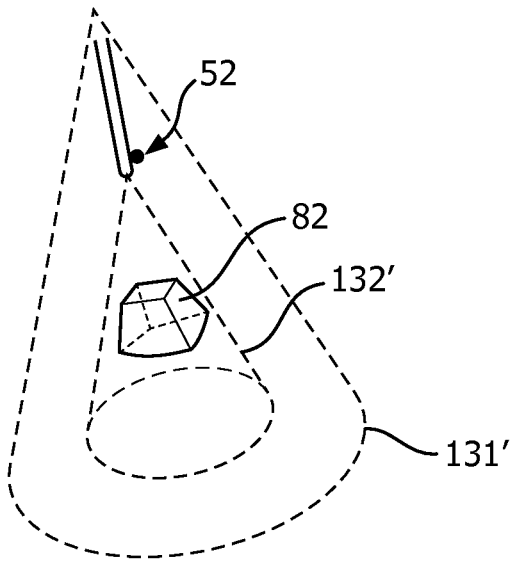
FIG. 11a          FIG. 11b
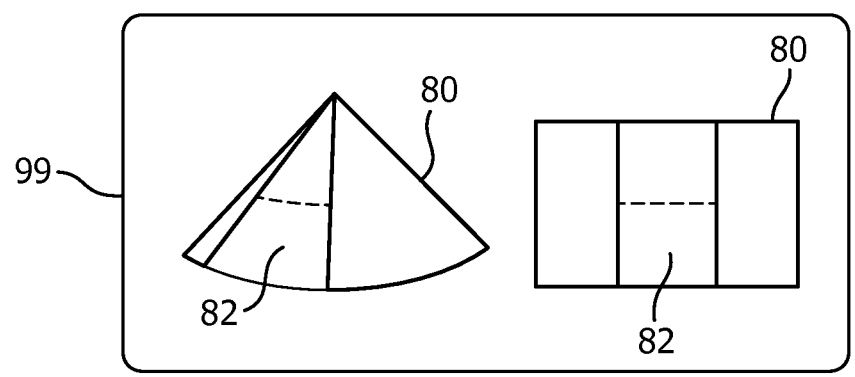
FIG. 12

ULTRASOUND SYSTEM FOR PROVIDING ULTRASOUND IMAGES AT VARIABLE FREQUENCIES OF A VOLUMETRIC REGION COMPRISING AN INTERFERER ANALYZER

This application is the U.S. National Phase application under 35 U.S.C. § 371 of International Application No. PCT/EP2016/076008, filed on Oct. 28, 2016, which claims the benefit of EP Application Serial No. 15192490.9,416, filed Nov. 2, 2015. These applications are hereby incorporated by reference herein.

FIELD OF THE INVENTION

The invention relates to an ultrasound system for providing an ultrasound image of a volumetric region comprising a region of interest comprising: a probe having an array of CMUT transducers, which array has a pitch value in at least one of azimuth and elevation dimensions and adapted to steer ultrasound beams in a variable frequency range over the volumetric region, wherein the beams are steered in at least one of azimuth and elevation steering angles; a beamformer coupled to the array and adapted to control the ultrasound beam steering and provide an ultrasound image data of the volumetric region; a transducer frequency controller coupled to the beamformer and adapted to vary operation frequencies of the CMUT transducers within the frequency range, which frequency controller is arranged to set the operation frequency to a first frequency for the ultrasound beam steered in the volumetric region and to change the operation frequency to a second frequency for the ultrasound beams steered within the region of interest, the second frequency being higher than the first frequency.

The present invention further relates to a method of variable frequency ultrasound imaging of a volumetric region using such an ultrasound system.

BACKGROUND OF THE INVENTION

An ultrasound imaging system with a CMUT transducer probe is known from WO2015028314 A1. This probe comprises an array having CMUT cells arranged to operate in either of the following modes: a conventional mode, wherein a DC bias voltage sets a CMUT membrane of the cell to vibrate freely above a cell floor during operation of the CMUT cell; and a collapsed mode, wherein the DC bias voltage sets the CMUT membrane of the cell to be collapsed to the cell floor during operation of the CMUT cell. An increase in the DC bias voltage results in an increase in a center frequency of the frequency response of the CMUT cell during the operation the collapsed mode, and a decrease in the DC bias voltage results in a decrease in the center frequency of the frequency response of the CMUT cell during the operation in the collapsed mode. The DC bias voltage can be selected for different clinical applications depending on the frequency at which a volumetric region of the body is imaged.

An implementation of the operating frequency variation in CMUT array may influence quality of the acquired ultrasound images.

There is need in new imaging techniques further utilizing the perspectives of the CMUT technology.

SUMMARY OF THE INVENTION

It is an object of the present invention to provide an ultrasound system, which enables improved capabilities in the ultrasound imaging.

This object is achieved according to the invention by providing an image processor responsive to the ultrasound image data, which is adapted to identify a location of a high intensity region within the volumetric region, said region of high intensity having signal intensity at least two times higher than the average intensity of the ultrasound image; and an interferer analyzer coupled to the transducer frequency controller, wherein said interferer analyzer is adapted to adjust at least one of beam steering parameters of the beams steered within the region of interest, when the second frequency is above a first threshold frequency value derived from the location of the high intensity region with respect to the steering angle.

The invention uses variable frequency capabilities of the CMUT transducers in providing a new imaging technique that allows increasing the frequency of the ultrasound beams within the identified region of interest. Once the ROI is identified in the ultrasound data, the transducer frequency controller increases the beam frequencies in a portion of the volumetric region in which the ROI is located. Depending of the steering angle of the beams and ultrasound wave frequency grating lobes may become apparent in the ultrasound data received from the ROI, wherein these lobes may originate from sources of the strong reflection located in the volumetric region. Usually the presence of these sources would manifest by apparent high intensity regions in the ultrasound image. The appearance of the grating lobes caused by the strong reflecting sources has a functional dependence on the direction of the steered beams within ROI and the location of strong reflectors with respect to the array's dimensions. The present invention provides the system capable of identifying locations of such sources based on signal intensity values originating from these sources. This is achieved by providing an image processor comparing intensities of the pixels in the ultrasound image with this image average intensity. Further, the interferer analyzer varies the beam steering parameters within ROI such that the influence of the grating lobs originating from the strong reflectors beyond the ROI is reduced. The advantage of the present invention that a wide view of the volumetric region with larger penetration depth and reduced spatial resolution; and a detailed field view of the ROI and higher spatial resolution can be produced using the same CMUT transducer array during a single ultrasound scan. The interferer analyzer would correct on potential image quality reduction in the detailed field view by adjusting the beam steering parameters. Therefore, a good quality of the ultrasound images can be achieved. In another words the system automatically instructs the beamforming control to minimize acoustic energy to be generated (or received) in the direction of the strong reflecting source when imaging the ROI by adjusting at least one of the beam steering parameters of the beams steered within the region of interest.

In an embodiment the interferer analyzer is further adapted to reduce the second frequency below a second threshold frequency value, being lower than the first threshold frequency value, wherein the second threshold frequency value corresponds to a transducer frequency for which an ultrasound wavelength is equal to the array pitch value multiplied by two.

The arrays' design may negatively influence a quality of the steered beam, when the operation frequency of the CMUT transducers becomes higher than a threshold value. The interferer analyzer, enables to mitigate the reduction in the acquired image quality (such as appearance of grating lobes) by adjusting one of the beam steering parameters of the beams steered within the region of interest if the relatively high frequency is above a threshold frequency value. A suitable beamsteering parameter to be adjusted is the ultrasound frequency of the beam, for example. Here, the ultrasound frequency is a central frequency of a main lobe of the ultrasound beam. Alternatively received signals corresponding to the received ultrasound echoes are filtered such that the frequency components that are known to be responsible for potential reduction of quality (grating lobes) in the ROI are removed.

Grating lobes may also occur when the array pitch, defined as an inter-transducer distance, is equal to or greater than half a wavelength of the ultrasound wave forming the beam and the beam is steered within an angle larger than a certain threshold. Therefore, not only the grating lobes caused by the presence of the strong reflectors but also grating lobes defined by the array's structural design may be taking into account by the interferer analyzer. The interferer analyzer may further reduce an influence of the grating lobes on the overall ultrasound image quality by further adjusting the beam steering parameters if the second frequency set by the transducer control crosses the second threshold value derived from a comparison of the ultrasound wavelength the array pitch. This provides achieving an improved acquisition conditions for the given array.

In further embodiment, the beam steering parameters comprise: ultrasound frequency, received signal spectrum filtration, azimuth and elevation steering angles.

One of the ways to reduce the grating lobes appearance for a given frequency is reducing the steering angle in azimuth and/or elevation directions. Alternatively, frequency of the steered beam may be reduced.

In yet another embodiment the ultrasound system further comprises a user interface coupled to the ROI identifier and responsive to a user manual selection of the ROI and the high intensity region within the volumetric region, the user interface is further adapted to adjust at least one of the beam steering parameters upon the user manual selection.

This gives the user an opportunity to manually select both the location of the ROI and the high intensity region in the ultrasound image. In addition, the user has a control over the beam steering parameters. If the user expects or observes a reduction in the ultrasound image quality, the control allows the user to further adjust the parameter manually.

In a further embodiment the user manual selection further comprises a frequency selection of the second and first frequencies from the variable frequency range; and a beam parameter selection, such as the azimuth and elevation steering angles.

The user interface can be also coupled to the frequency control, such that the user can also select the first and second frequencies from the variable frequency range. In case at least one of the selected frequency values is above the threshold value, the user interface provides a further possibility to manually reduce the set beam frequency or reduce the beam steering angles in both the azimuth and elevation steering directions.

In another embodiment the probe is an intracavity probe and the system further comprises a drive mechanism coupled to the probe which enables movement of the probe during imaging.

Such systems permit the intracavity probes to be moved with respect to the volumetric region giving additional flexibility to the user during the ultrasound imaging. The probe's movement can be combined with the beams adjustment for improved ultrasound imaging. This provides an automatic adjustment of the probe's position with respect to the volumetric region depending on the location of the ROI and optimal beam steering parameters.

In yet another embodiment the drive mechanism is adapted to move the probe with respect to the ROI location when the high intensity region is identified.

If the distance between the identified ROI and the probe is larger than the penetration depth of the acoustic beams at the selected increased frequency the system may arrange the drive mechanism to move the probe closer to the ROI, such that the detail view of the ROI with increased beam frequency may be produced. The probe's destination within the volumetric region may be optimized with respect to the location of the strong reflection sources, such that directions of the received grating lobes are excluded from the detailed field of view of the ROI.

In a further embodiment the array is a two-dimensional array or one-dimensional array.

Depending on the array's design the ultrasound system may be providing the three dimensional ultrasound images or two dimensional ultrasound images (slices) of the volumetric region.

BRIEF DESCRIPTION OF THE DRAWINGS

In the drawings:

FIGS. 11a-11b illustrate the scanning of the volumetric region with variable beam frequency using an intracavity probe adapted to be moved with respect to the volumetric region;

FIG. 12 illustrates display of ultrasound images obtained with an intracavity probe in accordance with the second embodiment of the present invention;

DETAILED DESCRIPTION OF EMBODIMENTS

Figure 1:
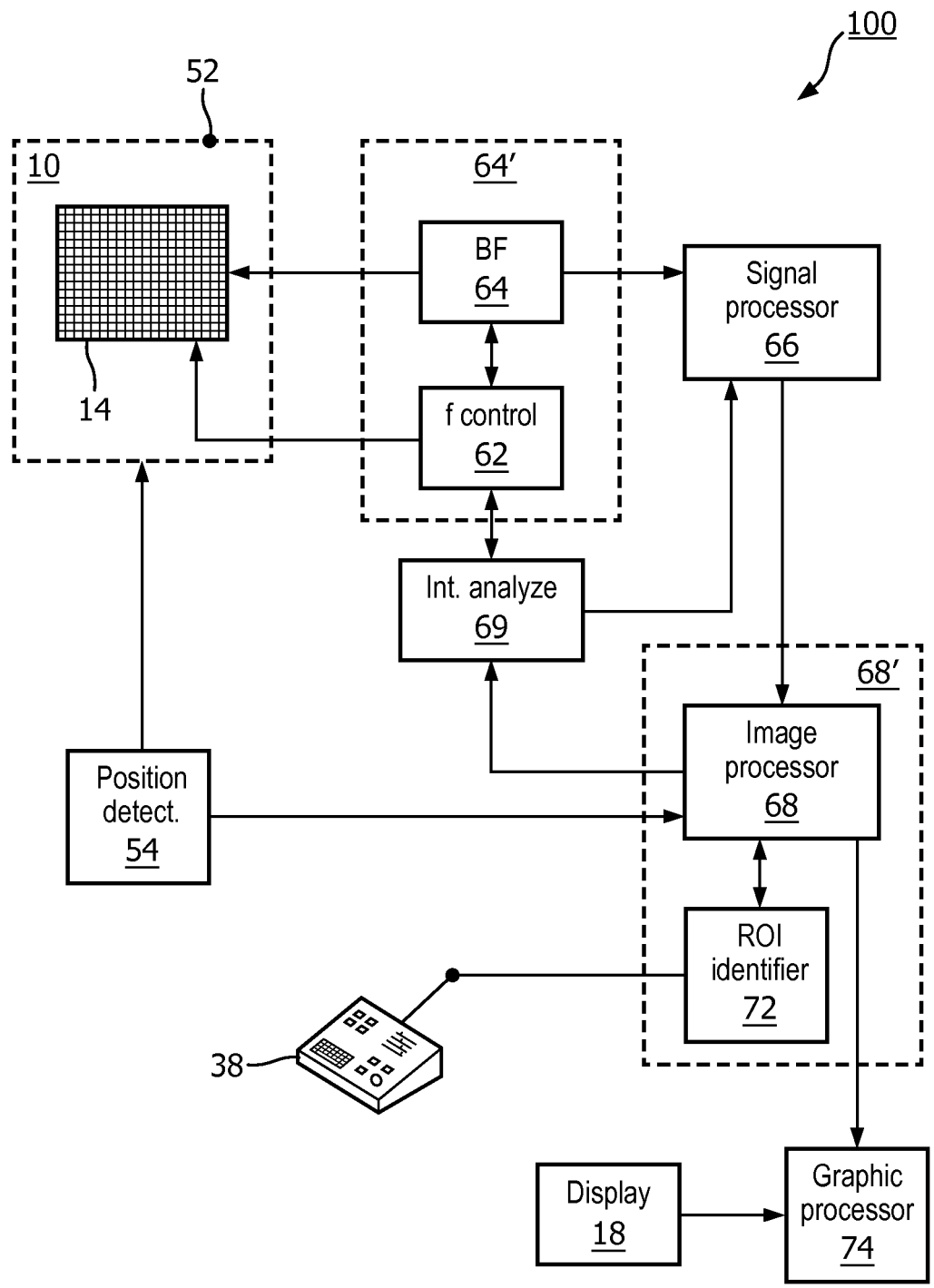
FIG. 1 illustrates an ultrasound system for variable frequency imaging of a volumetric region in accordance with the principles of the present invention.
Figure 2A:
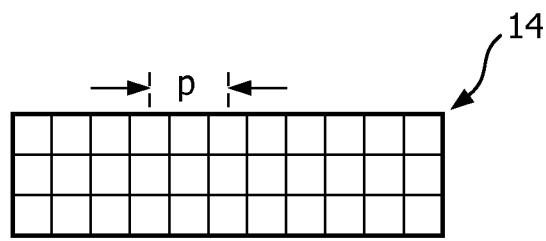
FIGS. 2a-2c show spatial orientation of steered beams with respect to the ultrasound array(s)
Figure 2B:
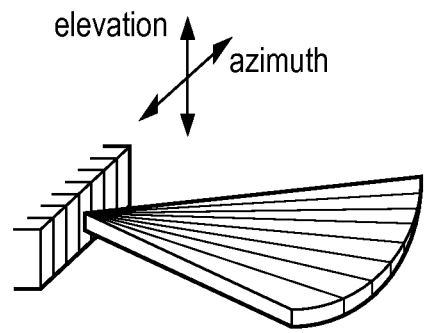
Figure 2C:
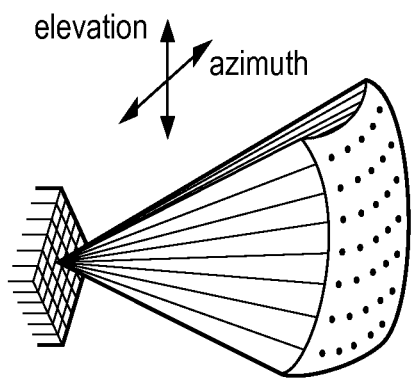
Figure 3:
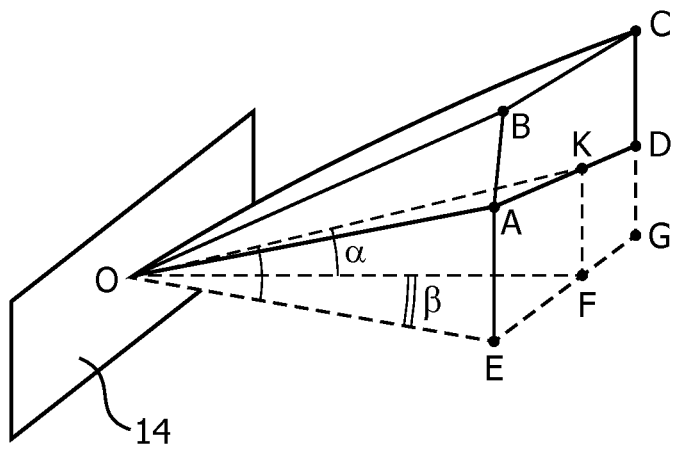
FIG. 3 illustrates beam steering parameters, such as steering angles, with respect to the array.

FIG. 1 shows schematically and exemplarily an ultrasound system 100 for variable frequency imaging of a volumetric region in accordance with the principles of the present invention. A probe 10 comprises an array 14 of variable frequency ultrasound transducers such as capacitive micromachined ultrasound transducers (CMUTs). This array 14 can be either two dimensional or one dimensional array. The CMUTs of the array transmit ultrasound beams in a variable frequency range over a volumetric field of view 131 (FIG. 9) (comprising the volumetric region) and receive echoes in response to the transmitted beams. The transducers of the array 14 transducer are coupled to a beamformer 64, which controls a steering of the ultrasound beams transmitted by the CMUTs of the array transducer 14. The transducer array can be 1D, 1.5D or 2D array. Depending on its dimensionality the array has at least one of azimuth and elevation dimensions (FIG. 2a). For the one-dimensional array (1D) the azimuth dimension coincides with the arrays dimension and defines an azimuth direction of a beam steering as shown in FIG. 2b. For two-dimensional (2D) array the azimuth and elevation dimensions define two orthogonal directions of the beam steering: azimuth and elevation directions as shown in FIG. 2c. The beamformer further beamforms echoes received by the transducers. Beams may be steered straight ahead from (orthogonal to) the transducer array 14, or at different angles for a larger field of view. An illustration of the beam steering angles for a 2D array is presented in FIG. 3. A pyramid OABCD represents a volumetric field of view, within which the beams are steered. Plane OKF is perpendicular to the array's 14 surface and parallel to the elevation direction, while plane OEF is perpendicular to both: the array 14 and OKF plane and is parallel to the azimuth direction. An azimuth steering angle (beta) of the beam is defined as an angle between the steered beam and the plane being perpendicular to the array and parallel to the elevation direction such as OKF plane. An elevation steering angle (alpha) of the beam is defined as an angle between the steered beam and the plane being perpendicular to the array and parallel to the azimuth direction such as OEF plane.

Optionally, the ultrasound system may have a plurality of microbeamformers (not shown) each coupling groups of the individual transducers with the beamformer 64. The microbeamfomers (sub-array beamformer) partially beamforms the signals from the groups of the transducers thereby reducing amount of signal channels coupling the probe and main acquisition system. The microbeamformers are preferably fabricated in integrated circuit form and located in the housing of the probe 10 near the array transducer. The probe 10 may further include a position sensor 52 which provides signals indicative of the position of the probe 10 to a transducer position detector 54. The sensor 52 may be a magnetic, electromagnetic, radio frequency, infrared, or other type of sensor.

The partially beamformed signals produced by the microbeamformers are forwarded to a beamformer 64 where these partially beam-formed signals from individual groups of transducers are combined into a fully beam-formed signal. The ultrasound system 100 further comprises a transducer frequency controller 62 coupled to the CMUT array 14 and the beamformer 64 (or optionally to the plurality of microbeamformers). The frequency control 62 controls the frequency of the transmitted and received ultrasound beams via adjusting a resonance frequency of each CMUT transducer in the array 14, as will be described more detailed below. The fully beam-formed signal (i.e. coherent echo signals along the beams) represent ultrasound image data, which are processed by filtering, amplitude detection, Doppler signal detection, and other processes by a signal processor 66. The ultrasound data are then processed into ultrasound image signals in the coordinate system of the probe by an image processor 68. The ultrasound image signals may be further converted to a desired ultrasound image format (x,y,z Cartesian coordinates, for example) by a graphic processor 74 and displayed on a display 18.

A region of interest identifier 72 is coupled to the image processor 68 and, based on analyses of the ultrasound image data, is adapted to identify a region of interest 82 within the volumetric field of view 131. Both the image processor 68 and the ROI identifier 72 can be a part of one image analyses unit 68'. The ultrasound imaging system 100 may be controlled by a user interface 38. In particular the user interface 38 can be connected to the ROI identifier 72 or directly to the image analyses unit 68' permitting a manual selection of the ROI 82' based on the ultrasound image displayed on the display. Further, a user via the user interface 38 can also select a desired frequency within a variable frequency range of the array, with which the user wishes the ROI to be imaged. This user input, such as location and size of the ROI 82' within the volumetric field of view 131 and the desired ROI imaging frequency, is communicated by the image analyses unit 68' to the transducer frequency controller 62. In the present embodiment the user identified parameters are exchanged between the ROI identifier 72 and the image processor 68, wherein the image processor computes coordinates of the ROI 82' and a volumetric region 132 surrounding the identified ROI in the volumetric field of view 131 based on identification data provided by the ROI identifier 72. The transducer frequency controller 62 is responsive to the identification data generated by the ROI identifier 72 and processed by the image processor 68. The transducer frequency controller 62 together with the beamformer adjusts the frequency of the beams steered within a volumetric region 132 surrounding the identified ROI in the volumetric field of view 131. In accordance with the principles of the present invention the ultrasound system 100 further comprises an interferer analyzer 69 coupled to the transducer frequency controller 62.

Owing to regular spacing of the array transducers, grating lobes exist in transmission and reception if the inter-element (inter-transducer) pitch is larger than an ultrasound wavelength. Thus, an increase in the imaging frequency may cause an appearance of grating lobes. These lobes carry ultrasound energy that spreads out from the transducer at angles other than intended beam paths. When the energy of the lobes is reflected by off-axis structures, such as strong reflectors, and detected by the transducer array, the signal produced is artefactual and causes "ghost images" blurring the main image. Therefore, a receiving beam formed for a given direction may have echo signals from the desired directions as well as directions of the grating lobes.

The receive-grating lobe angle depends on the (maximum) steering angle of the main beam, inter-element pitch, (ir)-regularity of the array, the number of transducers, their size, their operational frequency and bandwidth.

The inter-element pitch p is defined as an inter-transducer distance as shown in FIG. 2a. It is basically a distance between centers of the neighboring CMUT cells. Therefore, for a variable frequency transducer for a given array design the set frequency value may become larger that a threshold frequency value corresponding to the appearance of the grating lobes.

Figure 4:
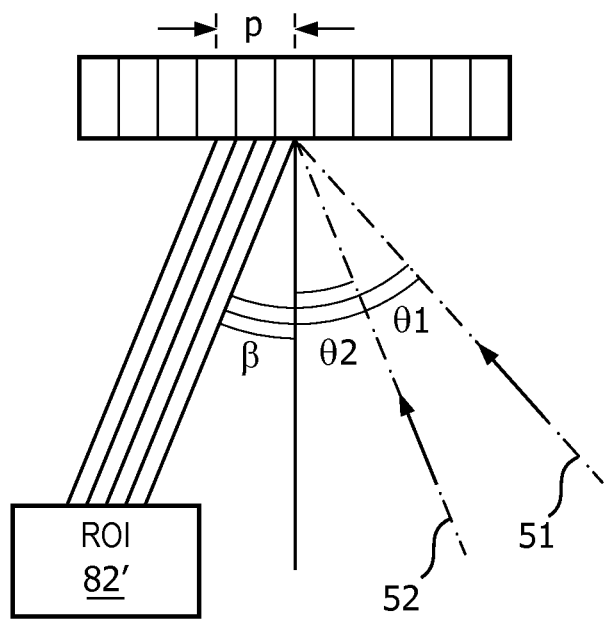
FIG. 4 illustrates a main receiving beam angle (13) steered within the ROI and associated different first order receive-grating lobe angles (0) at different frequencies.

FIG. 4 illustrates a linear transducer array having a main receiving beam angle (β) steered within the ROI (typically transmit beam angle is identical, not shown in this image) and associated different first order receive-grating lobe angles (θ) (typically, grating lobes happen as a result of transmit and receive steering angle). For a linear array transducer focusing in the far field, the direction (angle θ) of receiving grating lobes is $$\theta = \sin^{-1}\left(\sin\beta - \frac{m\lambda}{p}\right),$$

wherein m=±1, ±2, . . .

The wavelength λ can be expressed as $$\Delta = p(\sin\beta - \sin\theta) = Co/f,$$

wherein Co is the speed of ultrasound in the medium and f is a receive-signal frequency. In this example, the grating lobe angle is negative, while the steering beam angle is positive. Therefore, the receive-grating lobe angle θ (theta), the maximum receiving beam steered angle β (beta) and the pitch p are related to the receive-signal frequency f by:

$$f = \frac{Co}{p(\sin\beta - \sin\theta)}$$

At a cut-off frequency fc the grating lobes angle is −90 deg. Therefore, the threshold frequency at which the grating lobes angles would reach the transducer array at the angles beyond 90 degrees, would be in between Co/p for the maximum beam steering angle of 0 degree and Co/2p for the maximum beam steering angle of 90 degrees. This can be translated to a threshold wavelength being equal to the pitch of the transducer array or pitch multiplied by two. For a given steering beam direction (angle β) towards the ROI the grating lobe angle θ1 corresponding to the beam frequency f1 decreases to θ2 with frequency increasing to f2>f1, as shown in FIG. 4 with arrows 51 and 52. More details on grating-lobes can be found in A. Ponnle et al, *Suppression of grating lobe artifacts in ultrasound images*, Ultrasound in Med. & Biol., 681-691 (2013). In case a phased array is used, the value of "p" is different for phased arrays compared to linear arrays, because the maximum steering angle for phased arrays is larger than for linear arrays. In case of near field focusing the amplitude of the grating lobes is lower due to the irregularity of the delay differences of waves arriving on the receiving transducers.

The interferer analyzer 69 is adapted to compare the operational frequency of the array set by the transducer frequency controller 62 with the threshold frequency of this array. Once the set operational frequency reaches the threshold, the interferer analyzer 69 via the beamformer 64 can vary at least one of the beam steering parameters of the beams steered with this operational frequency.

The beam steering parameters comprise ultrasound frequency or spectral filtering of the received ultrasound signals. For example, a broad band ultrasound signal transmission can be used. The received signals are filtered by the signal processor afterwards such that the frequency components that are known to be responsible for potential grating lobes in the ROI are removed. The beam steering parameters also include beam steering angle in azimuth and/or elevation directions. The interferer analyzer via the beamformer may reduce the grating lobes by decrease the azimuth (beta) and/or elevation (alpha) steering angle within the volumetric region 132 while maintaining the wide axial depth to avoid grating lobes. Eliminating grating lobes also improves the signal-to-noise ratio by increasing the size of the main lobe energy relative to the background energy. This further improves image contrast. This provides achieving an optimal acquisition conditions for the given array.

The beamformer 64 and the transducer frequency controller 62 can be designed as one variable frequency beamformer unit 64' combining the frequency variation and beamforming capabilities. In the alternative embodiment, the microbeamformer may be combined together with the transducer frequency controller 62 into the variable frequency beamformer unit 64' and may be located within a housing of the probe.

Figure 5:
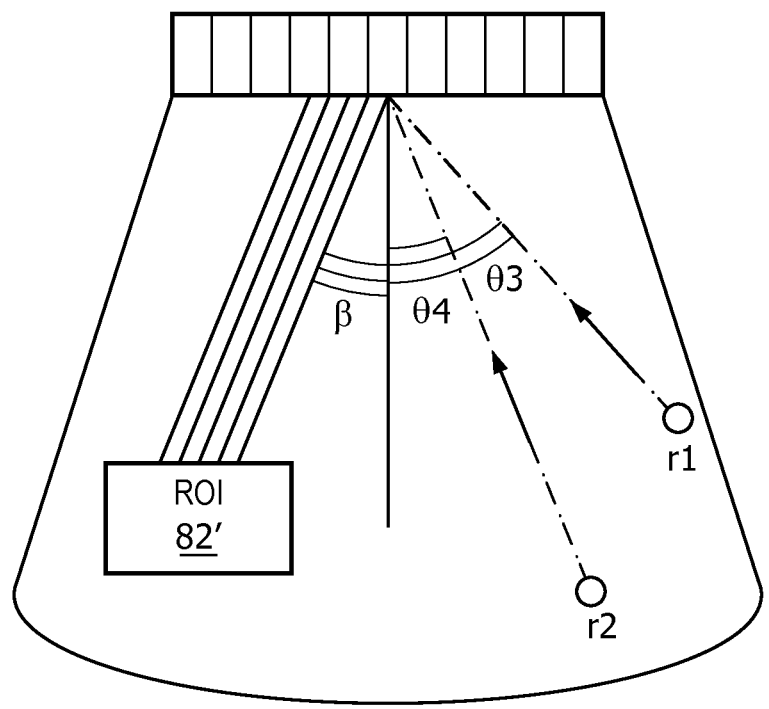
FIG. 5 illustrated steered ultrasound beams within a slice of the volumetric region and associated different first order receive-grating lobe angles (0) at different frequencies.

In another embodiment of the present invention the image processor is adapted to process the ultrasound image data and identify a location of a high intensity region within the volumetric region. If the volumetric region has sources of the high intensity reflection (strong reflectors), these source would appear in the ultrasound image data as the regions of high intensity. Usually the intensity of these regions would manifest with values at least 5 to 10 times higher than average intensity of the processed ultrasound data. The identified location of the strong reflectors, for example r1 and r2 in FIG. 5 are analyzed by the interferer analyzer 69, which is further adapted to compare the directions (characterized with angles θ4 and θ5) of the reflected ultrasound echoes, originating from the reflectors, with the main beam steering angle β at the operation frequency used to scan the ROI. In this embodiment the smallest angle θ (in the present example θ4), would determine the threshold frequency at which the best quality image of the ROI may be acquired. An alternative is to "avoid" the critical frequency, so stay well below or well above the critical frequency. The interferer analyzer 69 further adapts the beam steering parameters of the beams steered within the ROI, such that the effect of the grating lobes originating from the strong reflectors is mitigated. For example, this can be done by reducing the frequency of the beams within the ROI below the threshold value; or the interferer analyzer 69 may communicate to the signal processor 66 a set of frequencies at which the strong reflectors may contribute to the received ultrasound signals, such that the signal processor 66 can filter these frequencies out of the received signals.

In accordance with the present invention the variation of the ultrasound beam frequency of the ultrasound system is provided using CMUT transducers adapted to operate in a collapsed mode. CMUT technology allows the tuning of the imaging frequency by changing the bias voltage. This frequency range extends over a broad range and on top of this range at each frequency there is also a bandwidth which for a substantial part is close to or even exceeding 100%. This large frequency variability allows for imaging over a wide range of penetrations and resolutions.

Figure 6:
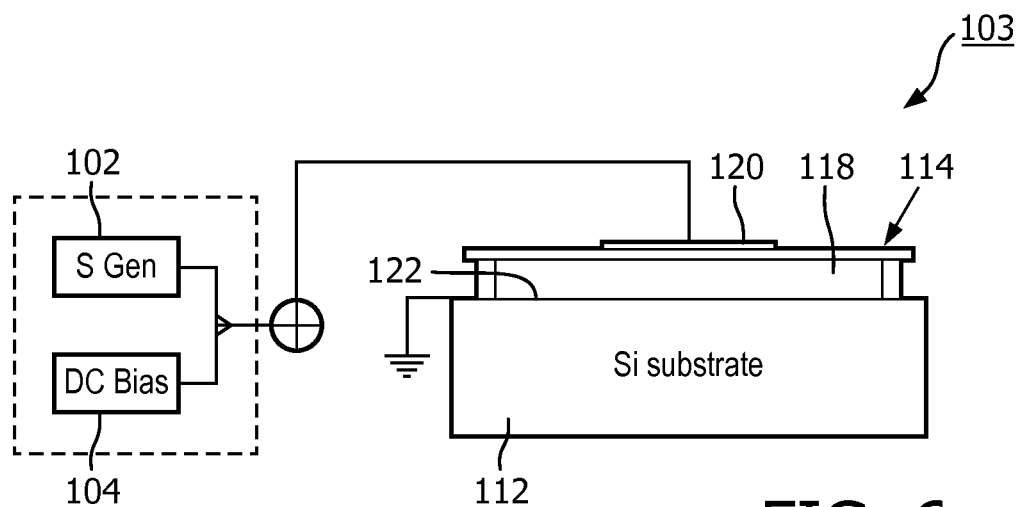
FIG. 6 illustrates a CMUT cell controlled by a DC bias voltage and driven by an rf. drive signal.

The CMUT transducer array 14 of the present invention comprises a plurality of CMUT cells (transducers). In FIG. 6 each CMUT cell 103 typically comprises a flexible membrane or diaphragm 114 suspended above a silicon substrate 112 with a gap or cavity 118 there between. A top electrode 120 is located on the diaphragm 114 and moves with the diaphragm. A bottom electrode is located on the floor of the cell on the upper surface of the substrate 112 in this example.

Other realizations of the electrode 120 design can be considered, such as electrode 120 may be embedded in the membrane 114 or it may be deposited on the membrane 114 as an additional layer. In this example, the bottom electrode 122 is circularly configured and embedded in the substrate layer 112 by way of non-limiting example. Other suitable arrangements, e.g. other electrode shapes and other locations of the bottom electrode 122, e.g. on the substrate layer 112 such that the bottom electrode 112 is directly exposed to the gap 118 or separated from the gap 118 by an electrically insulating layer or film to prevent a short-circuit between the top electrode 120 and the bottom electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 6 the bottom electrode 122 is grounded by way of non-limiting example. Other arrangements, e.g. a grounded top electrode 120 or both top electrode 120 and bottom electrode 122 floating are of course equally feasible.

The cell 100 and its cavity 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 103 shall be understood as the biggest lateral dimension of the cell.

The bottom electrode 122 may be insulated on its cavity-facing surface with an additional layer (not pictured). The components of the CMUT cell may be fabricated from CMOS compatible materials, e.g., Al, Ti, nitrides (e.g., silicon nitride), oxides (various grades), tetra ethyl oxysilane (TEOS), poly-silicon and the like. In a CMOS fabrication, for example, the oxide and nitride layers may be formed by chemical vapor deposition and the metallization (electrode) layer put down by a sputtering process.

Suitable CMOS processes are LPCVD and PECVD, the latter having a relatively low operating temperature of less than 400° C. Exemplary techniques for producing the disclosed cavity 118 involve defining the cavity in an initial portion of the membrane layer 114 before adding a top face of the membrane layer 114. Other fabrication details may be found in U.S. Pat. No. 6,328,697 (Fraser).

In FIG. 6, the diameter of the cylindrical cavity 118 is larger than the diameter of the circularly configured electrode plate 122. Electrode 120 may have the same outer diameter as the circularly configured electrode plate 122, although such conformance is not required. Thus, the membrane electrode 120 may be fixed relative to the top face of the membrane layer 114 so as to align with the electrode plate 122 below. The electrodes of the CMUT cell 100 provide the capacitive plates of the device and the gap 118 is the dielectric between the plates of the capacitor. When the diaphragm vibrates, the changing dimension of the dielectric gap between the plates provides a changing capacitance which is sensed as the response of the CMUT cell 100 to a received acoustic echo.

The spacing between the electrodes is controlled by applying a static voltage, e.g. a DC bias voltage, to the electrodes with a voltage supply 45. The voltage supply 45 is implemented into the transducer frequency controller 62 and provides its frequency control capabilities. The transducers of the array 14 each may have a separate voltage supply or share several voltage supplies implemented in the transducer frequency controller 62. The voltage supply 45 may also optionally comprise separate stages 102, 104 for providing the DC and AC or stimulus components respectively of the drive voltage of the CMUT cells 103. The first stage 102 may be adapted to generate the static (DC) voltage component and the second stage 104 may be adapted to generate an alternating variable voltage component or stimulus having a set alternating frequency, which signal typically is the difference between the overall drive voltage and the aforementioned static component thereof. The static or bias component of the applied drive voltage preferably meets or exceeds the threshold voltage for forcing the CMUT cells 103 into their collapsed states. This has the advantage that the first stage 102 may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component. Other suitable embodiments of the voltage source supply 45 should be apparent, such as for instance an embodiment in which the voltage source supply 45 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage source supply 45 may be implemented in any suitable manner.

As is known per se, by applying a static voltage above a certain threshold, the CMUT cell 103 is forced into a collapsed state in which the membrane 114 collapses onto the substrate 112. This threshold value may depend on the exact design of the CMUT cell 103 and is defined as the DC bias voltage at which the membrane 114 sticks to (contacts) the cell floor by Van der Waal force during the application of the bias voltage. The amount (area) of contact between the membrane 114 and the substrate 112 is dependent on the applied bias voltage. Increasing the contact area between the membrane 114 and the substrate 112 increases the resonance frequency of the membrane 114, as will be explained in more detail with the aid of FIG. 7*a-d*.

Figure 7A:
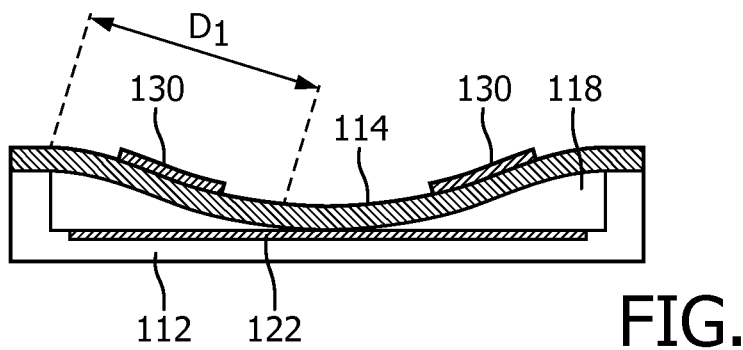
FIGS. 7a-7d illustrate the principles of collapsed mode CMUT operation applied in an implementation of the present invention.
Figure 7B:
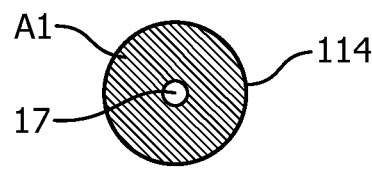
Figure 7C:
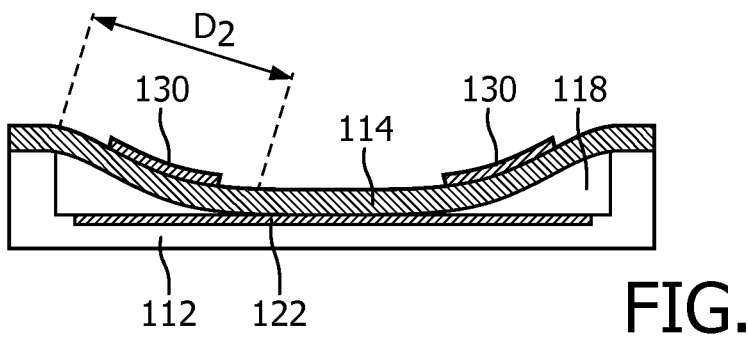

The frequency response of the collapsed mode CMUT cell 103 may be varied by adjusting the DC bias voltage applied to the CMUT electrodes after collapse. As a result, the resonant frequency of the CMUT cell increases as a higher DC bias voltage is applied to the electrodes. The principles behind this phenomenon are illustrated in FIGS. 7*a* and 7*b*. The cross-sectional views of FIGS. 7*a* and 7*c* illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 7*a* when a relatively low bias voltage is applied, whereas the distance D2 in FIG. 7*c* is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 7*a* will be lower than the resonant frequency of the CMUT cell in FIG. 7*c* which is subject to the higher pulldown bias voltage.

Figure 7D:
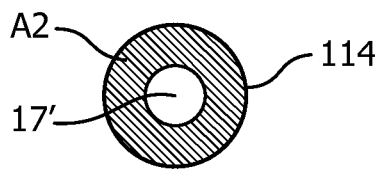

The phenomenon can also be appreciated from the two-dimensional illustrations of FIGS. 7*b* and 7*d*, as it is in actuality a function of the effective operating area of the CMUT membrane. When the membrane 114 just touches the floor of the CMUT cell as shown in FIG. 7*a*, the effective vibrating area A1 of the non-contacting (free vibrating)

portion of the cell membrane 114 is large as shown in FIG. 7b. The small hole in the center 17 represents the center contact region of the membrane. The large area membrane will vibrate at a relatively low frequency. This area 17 is an area of the membrane 114, which is collapsed to the floor of the CMUT cell. But when the membrane is pulled into deeper collapse by a higher bias voltage such as in FIG. 7c, the greater central contact area 17' results in a lesser free vibrating area A2 as shown in FIG. 7d. This lesser area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

Figure 8:
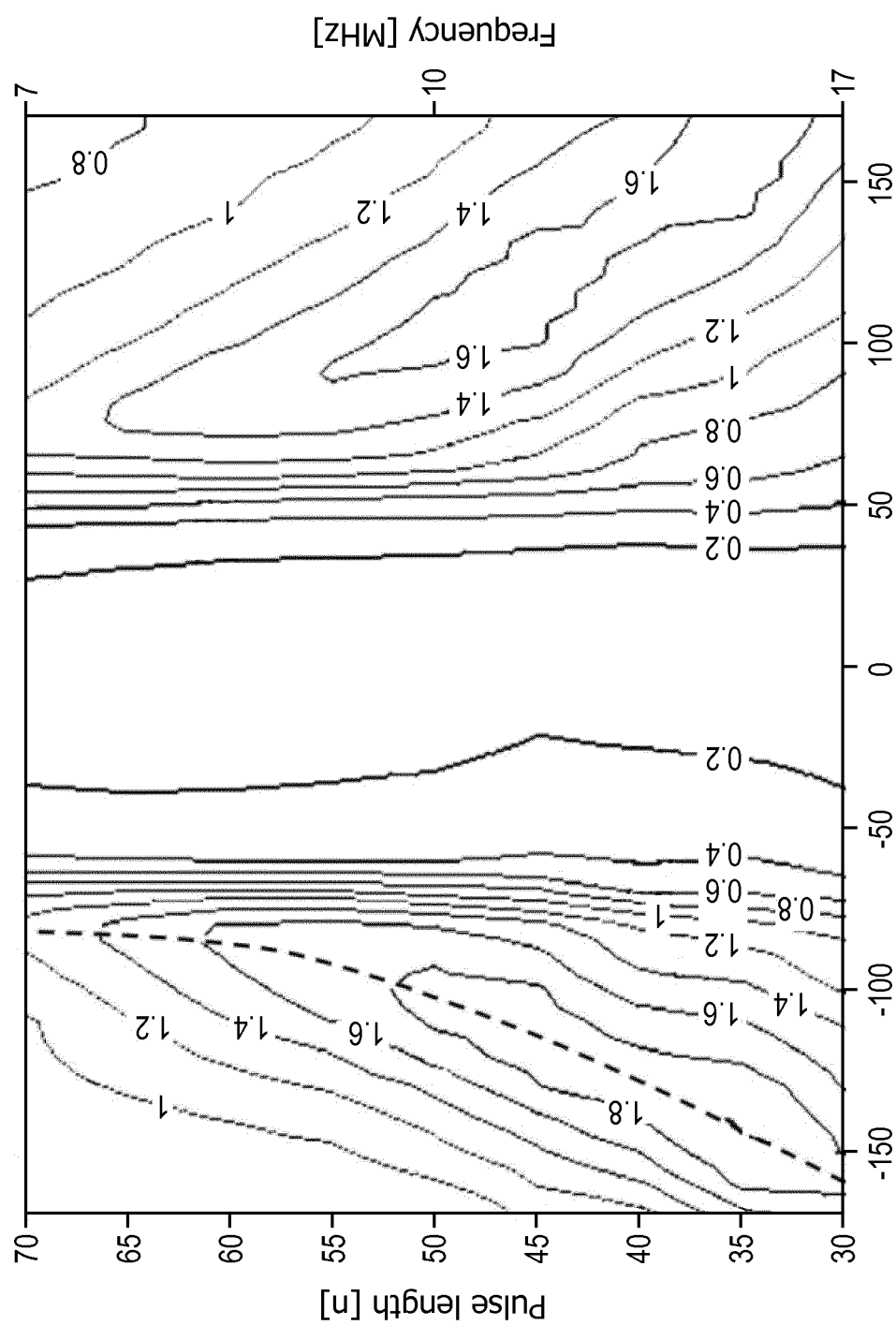
FIG. 8 illustrates a contour plot of the acoustical performance of such the CMUT cell operating in collapsed mode.

FIG. 8 shows a contour plot of the acoustical pressure output of a typical CMUT cell 103 in collapse mode as a function of applied DC bias voltage including a stimulus in the form of an AC modulation or frequency modulation of constant frequency during transmission. The corresponding pulse length is half the applied frequency. As can be seen from this contour plot, when the CMUT cell 103 is operated at a fixed or static voltage, e.g. a DC bias voltage of static value, optimal acoustic performance is obtained for a small range of frequencies only. However, when varying the bias voltage and the frequency modulation on the bias voltage signal in a correlated manner, as indicated by the dashed line in the contour plot, the optimal acoustic performance of the CMUT cell 103 may be achieved over a much larger frequency range, thereby increasing the effective bandwidth of the ultrasound pulse (or pulse train) generated in the transmission mode of the ultrasound probe including the CMUT cell 103. Thus, frequency can be varied in a frequency range from 7 to 17 MHz, as in this example; 3 to 10 MHz; or even larger frequency range expanding from 2 to 15 MHz.

This can be understood in back reference to FIGS. 7a and 7d, which explained that the resonance frequency of the CMUT cell 103 in a collapsed state is a function of the applied (DC) bias voltage. By adjusting the applied bias voltage when generating ultrasonic pulses of a particular set frequency by applying a stimulus having the appropriate set frequency, pulses of different frequencies can be generated exhibiting (near-)optimal acoustic performance of the CMUT cell 103 for each pulse frequency. This therefore ensures (near-) optimal imaging resolution over a large bandwidth of the imaging spectrum.

Acoustic wave attenuation increases with increasing frequency, while ultrasound image resolution reduces with increasing frequency. For example, a typical depth and axial resolution for a two-cycle pulse in tissue is given in the table below:

| Frequency (MHz) | Image depth (cm) | Axial resolution (mm) |
|---|---|---|
| 2 | 30 | 0.77 |
| 5 | 12 | 0.31 |
| 7.5 | 8 | 0.2 |
| 10 | 6 | 0.15 |
| 15 | 4 | 0.1 |

To meet optimal and penetration requirements reasonably, the frequency range for most diagnostic applications is 2 to 15 MHz. The lower portion of the range is useful when increased depth (e.g., the region of interest is located deeper in body) or high attenuation (e.g., in transcranial studies) is encountered. The higher portion of the frequency range is useful when little penetration is required (e.g. in imaging breast, thyroid, or superficial vessel or in pediatric imaging). In most large patients, 3-5 MHz is a satisfactory frequency, whereas in thin patients and in children, 5 and 7.5 MHz often can be used. A higher frequency range above 15 MHz can provide high resolution imaging using intracavity (intravascular) probes, such as IVUS, ICE, FL-ICE. These probes can be positioned closer to the ROI inside body cavities, vessel, etc.

The present invention provides a unique combination of a variable frequency ultrasound imaging in a broad frequency range using a single array 14 of the CMUT transducers.

Figure 9:
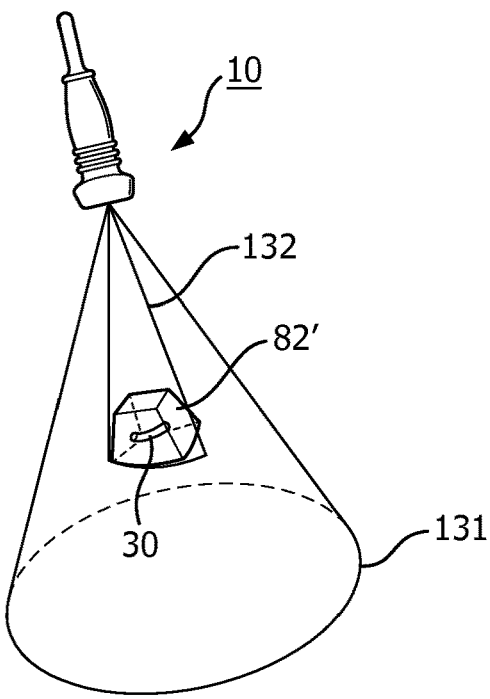
FIG. 9 illustrates the scanning of the volumetric region with a relatively low frequency of the ultrasound beams steered within the volumetric region and a relatively high frequency of the ultrasound beams steered within the region of interest.

FIG. 9 illustrates an implementation of the present invention, wherein the probe's position with respect to the ROI is fixed. The probe 10 is used to acquire ultrasound images of the volumetric field of view 131. The transducer frequency controller 62 is responsive to the region of interest identifier 72 sets a relatively low frequency (first frequency) of the ultrasound beams steered within the volumetric field of view 131 and a relatively high frequency (second frequency) of the ultrasound beams steered within the volumetric region 132 surrounding the identified ROI 82'. The interferer analyzer 69 compares the second frequency to the threshold frequency value. The threshold frequency value either can be input manually via the user interface 38 or automatically recognized by the ultrasound system 100, once the probe 10 with the given array is coupled to the system 100. If the operational frequency value is above the threshold frequency, the interferer analyzer 69 adjusts the beam steering parameters such that the influence of the received-grating lobes is reduced to minimum at the given imaging conditions. For example, the second frequency value may be reduced below the threshold value.

The received by the CMUTs echoes are beamformed by the beamformer, which provides the ultrasound image data of the volumetric region having a relatively low spatial resolution within the volumetric region and relatively high spatial resolution within the region of interest. These ultrasound data are processed in the image processor 68, wherein a wide view 80 of the volumetric region based on the low spatial resolution data and a detail view 132' of the region of interest 82 based on the high spatial resolution data are produced as shown in FIG. 10. The detail view 132' of the volumetric region 132 surrounding the identified ROI 82 may also comprise an image 133 of the area located in between the probe and the ROI. FIG. 10 illustrates a display 99 of 2D ultrasound images displayed to the user with the wide view 80 and the detail view 132' in spatial registration with respect to each other. The selected ROI 82 is displayed at the increased imaging frequency in the detail view 132'. Since the penetration depth of the ultrasound beams with relatively high frequency is reduced compared to the penetration depth of the ultrasound beams with the relatively low frequency, an upper frequency limit of the relatively high frequency range will be limited by a depth (distance to the probe) at which the ROI is located and will be taken into account by the image processer 68 during its computation. An additional limitation to the upper second frequency (and therefore to the penetration depth) is imposed by the threshold frequency calculated by the interferer analyzer 69. This would hold for this embodiment, wherein the probe's position with respect to the ROI is fixed. The system 100 may first acquire ultrasound data of the volumetric field of view with the relatively low beam frequencies, thus providing surrounding context of the volumetric region, and further "zoom-in" to the ROI 82' upon its identification. At this stage the obtained low frequency image would be also processed in order to identify the strong reflectors, the beam steered within the identified ROI, would be adjusted in accordance to the optimal ultrasound image acquisition.

The detail view 132' can be updated in the real time next to the wide view 80 acquired previously and displayed for the context as illustrated in FIG. 6c. The user interface 38 manual selection further comprises a frequency selection of the relatively low and the relatively high frequencies from the variable frequency range; and a beam steering parameter selection, such as the azimuth and elevation steering angles. Via the user interface 38 the user may also manually select the locations of the strong reflectors in the wide view, which locations are further used by the interferer analyzer. The interferer analyzer 69 in communication with the image processor may estimate the expected ultrasound image quality including the penetration depth for a set of threshold frequencies. These set may comprise frequencies derived from: the ultrasound wavelength being equal to the array pitch value and from the location(s) of the high intensity region with respect to the steered beams. These set with corresponding ultrasound image quality be given to the user. The user can further select a threshold frequency for the given workflow. For example, a trade off may be made in between an increasing the field of view and further reducing the frequency below the threshold value or decreasing the field of view but keeping the frequency above the threshold value. In the latter case, high resolution images with more artifacts may be obtained. This way the user has an additional control over the beam steering parameters and may further manually adjust the steering angles of the beams in either of the directions, change the beams frequency or received signal filtering.

Alternatively, the detail view 132' of the ROI 82 and the wide view 80 can be displayed next to each other. In cardiology application during heart imaging the display and acquisition of the ultrasound images may be synchronized with heart cycle by an ECG gating.

Figure 10A:
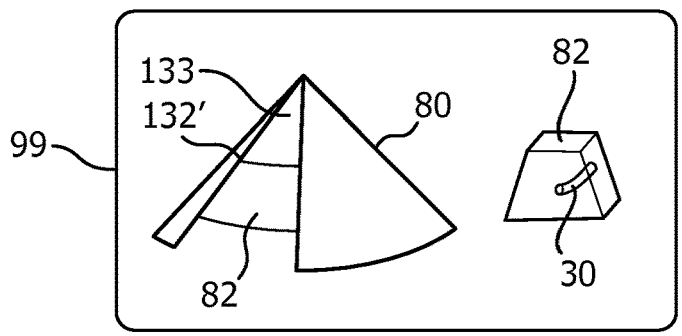
FIGS. 10a-10c illustrate displays of ultrasound images of a volumetric region together with the wide view of the volumetric region comprising the detail view of the region of interest.
Figure 10B:
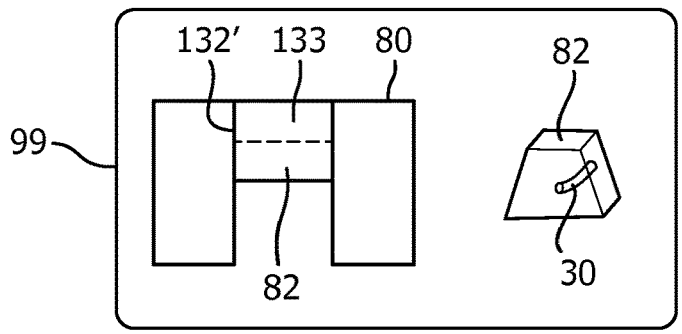
Figure 10C:
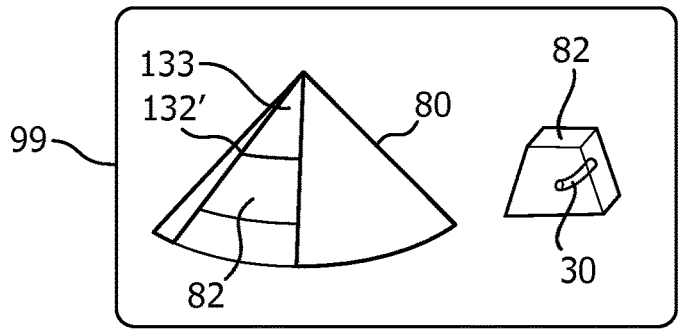
Figure 13:
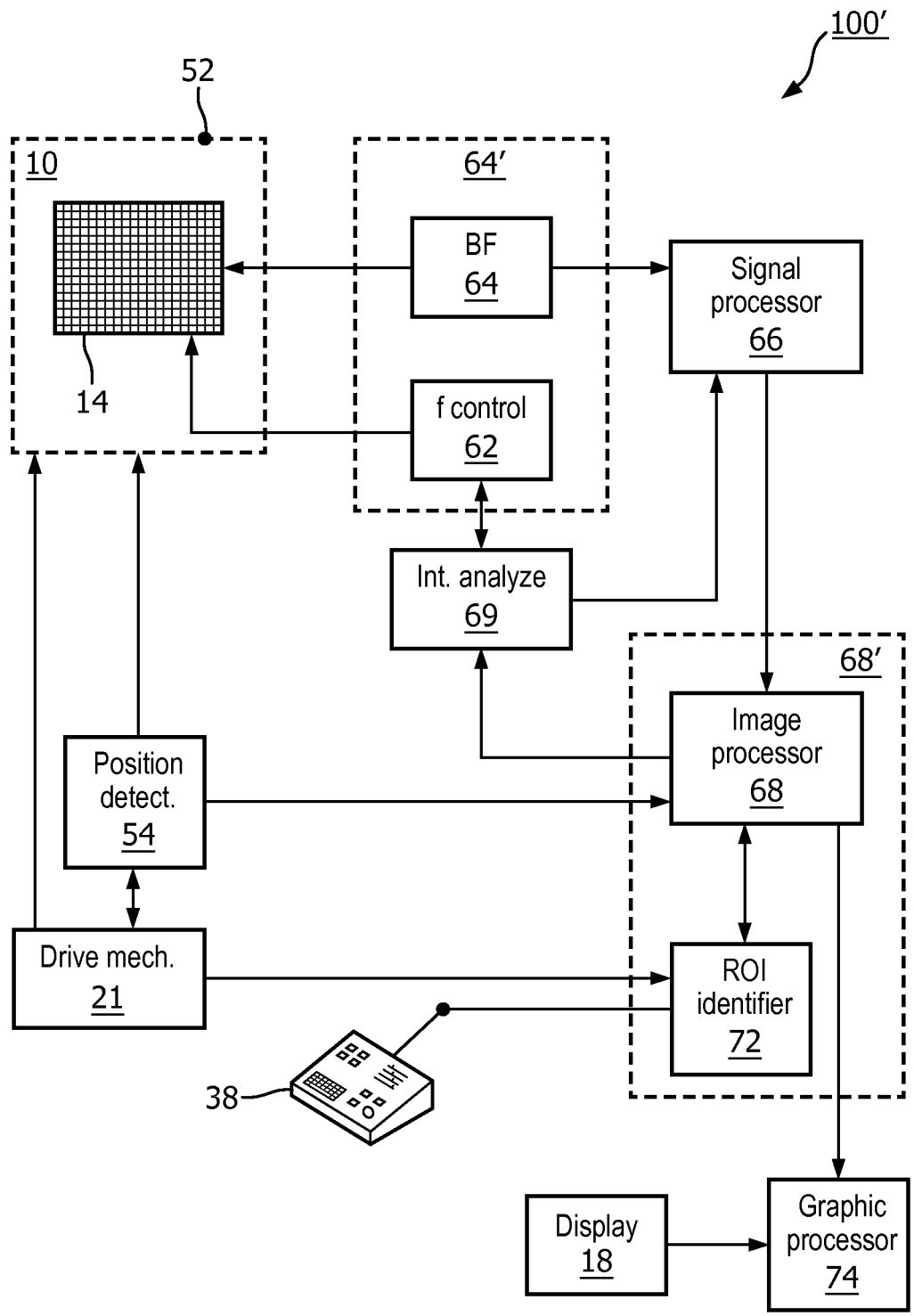
FIG. 13 illustrates an ultrasound system for imaging a volumetric region comprising a region of interest in accordance with another embodiment of the present invention.

In case the CMUT array 14 is a linear arrays the transducer frequency controller 62 can address (drive) the individual transducer cells 103 with different frequencies so that the ROI is imaged at high frequency and that the other elements are maintained at low frequencies. A representative image acquired with the linear array is shown in FIG. 10b. An embedded real time high frequency detail view 132' image is generated simultaneous to a real time low frequency wide view 80 image. This has the advantage that the surrounding context is still imaged (albeit at lower solution) in real time with relatively higher depth to allow for example orientation and navigation of tools that occur in the periphery of the ROI. It is also possible to obtain similar images if the CMUT array 14 is a phased array as shown in FIG. 10a and FIG. 10c. In the phased array case the beamforming is performed such that for each line that constitutes the image, an appropriate frequency for all the transducers is chosen such that a high frequency detail view 132' image is imbedded in the wide view 80 image containing lower frequency lines. If both views: the detail view 132' of the ROI 82' and the wide view 80 are updated in real time, the system comprising the phased array can continually acquire first all lines of the volumetric field of view 131 volume at low frequency and then all lines the volumetric region 132 surrounding the identified ROI 82 with higher frequency. The acquired view can by further interleaved or interpolated into one ultrasound image. This is illustrated in FIG. 6c. In alternative acquisition workflow the wide view 80 is updated beyond detail view 132', wherein the resulting image displayed to the user is illustrated in FIG. 6a. The former has the advantage of real time views of the whole volume eg. to track interventional devices. The latter has the advantage that less lines are acquired and a higher frame rate can be achieved.

FIG. 11 illustrates second embodiment of the present invention, wherein the probe's position can be varied within the volumetric field of view 131'. The probe, for example, can be placed in a forward looking or end firing configuration such that the probe can be easily translatable towards and away from the ROI. This can be realized by providing the intracavity probe such as IVUS, ICE, FL-ICE, for example as described in EP1742580B. The intracavity probe may include the transducer array in the distal tip which is swept to scan a volumetric region. The volume sweeping can be done either providing a mechanical movement of the 1D array or an electronic steering of the beams with the 2D array. The transducer array is contained within a fluid chamber located at the distal tip of the probe, wherein fluid provides an appropriate acoustic coupling between the probe and the imaged volumetric region. In FIG. 12 the ultrasound system 100' is schematically shown. The system 100' may further comprise a drive mechanism 21 coupled to the probe and the ROI identifier 72 (optionally to the analyses unit 68'), wherein the drive mechanism acts to move the probe 10 during imaging. The drive mechanism 21 also receives the signals from the position sensor 52, which tracks the probe's spatial location, thus providing the probe's movement within the volumetric field of view 131'. This embodiment gives a higher flexibility to the upper limit of the high frequencies with which the ROI 82 can be imaged. Once the ROI is identified the image processor 68 computes coordinates of the ROI 82 and a volumetric region 132 surrounding the identified ROI in the volumetric field of view 131 based on identification data provided by the ROI identifier. If the distance between the transducer array 14 (or practically the probe 10) and the ROI is beyond the penetration depth of the beams with the selected high frequency (provided that this frequency is below the threshold frequency value), the drive mechanism 21 would be communicated to move closer towards the ROI within the volumetric field of view 131' (FIG. 11b), such that a "zoom-in" image of the ROI cab be acquired. The interferer analyzer 69 identifies that the relatively high frequency (the second frequency) is above one of the threshold frequency values derived from: the ultrasound wavelength being equal to the array pitch value and/or from the location(s) of the high intensity region with respect to the steered beams. The drive mechanism may adapt the distance with respect to the ROI based on a calculated penetration depth corresponding to the smallest identified threshold frequency value. Alternatively, the user may select the desired image quality and corresponding to it distance to the ROI. This embodiment may have a better implementation of the beam steering angle adjustments, since the ultrasound array can be moved with respect to the ROI, while simultaneously reducing the steering angles of the beams within the ROI.

FIG. 12 illustrates a display 99 of 2D ultrasound images displayed to the user. Similarly to the first embodiment the detailed 82 and wide fields of view 80 may be shown either next to each other or in a spatial registration. The latter case is illustrated in FIG. 12, wherein the images obtained with the linear and phased arrays are placed next to each other. Compared to FIGS. 6a-b the detail view 82 would appear to the user as having a larger penetration depth compared to the embodiment, wherein the probe's position is fixed with respect to the ROI's location. The detail view image can be continuously acquired during the probe's progression (movement), such that the wide view image 80 can be real-time updated with higher resolution detailed view images 82 acquired at different points of time.

Based on the ROI identification and the user identified parameters the image processor 68 may analyze the obtained ultrasound data for image quality parameters such as axial noise, lateral speckle, axial intensity etc. These quality parameters may be further displayed to the user. These quality parameters can also be used as an input to the drive mechanism to automatically move the probe so that it can be part of a feedback loop for automatic optimization of the ROI image quality. Such automation may be used for a fine movement of the probe, while the gross motion can be controlled via the user interface.

The quality parameters of the ultrasound image would be also determined by the beam steering parameters adjusted by the interferer analyzer 69. Via the user interface 38 the user can be provided an additional control on the drive mechanism operation and the beam steering. The user interface can be a touch screen associated with the display, which permits the user to manually define in a displayed image the ROI, probe's movement and the regions of strong reflection. Touching on the ROI and/or making the "pinch-in" or "pinch-out" movement can be used to physically move the probe in a certain direction(s) or acquires the detailed image if the penetration depth is sufficient for the given probe's position.

In an alternative embodiment a real time detailed 3D field of view of the ROI obtained with relatively high frequency is imbedded within a wide view 2D image. This has the advantage that acquiring the wide view 2D image consumes less processing power and transducer utilization and that the 3D image (or biplane ROI) can be obtained at the highest possible frame rate. For the arrays with small aperture in one dimension (e.g., ICE), this embodiment provide the wide view imaging based on the more favorable aperture dimensions (ICE axial, and lateral) and the detailed ROI imaging at all dimensions (e.g. ICE: including elevation), which becomes more favorable at high frequency.

The ROI identifier can identify the ROI automatically using ultrasound data from a specific object such as a catheter, needle or tool which can optionally be marked with ultrasound enhancing contrast features. These objects by virtue of their geometry and aspect (or markers or positional sensor) can be recognized by the image analyses unit 68' and the coordinates of the ROI can be automatically generated.

In another embodiment an image of a volume of interest can be acquired initially with relatively high frequency beams, this volume of interest can be identified by the user as the ROI. Further, the user via the user interface can decrease the imaging frequency, relative to what was used for the ROI, in order to obtain a wide view image with higher penetration depth, wherein the wide view image comprises the ROI. Similar to previous embodiments these fields of view may be displayed either next to each other or in the spatial registration.

Separate requirements may be imposed onto an integrated circuit (IC) electronics of the variable frequency beamformer unit 64' (or optionally of the transducer frequency controller 62) in order to provide an optimal speed of the bias-voltage change applied to the CMUTs. For most instances described above current IC electronics technology may be sufficient. Alternatively, in case even larger speed of the bias-voltage change is needed the 3-terminal CMUT as described in WO/2015/086413 in may be used.

Figure 14:
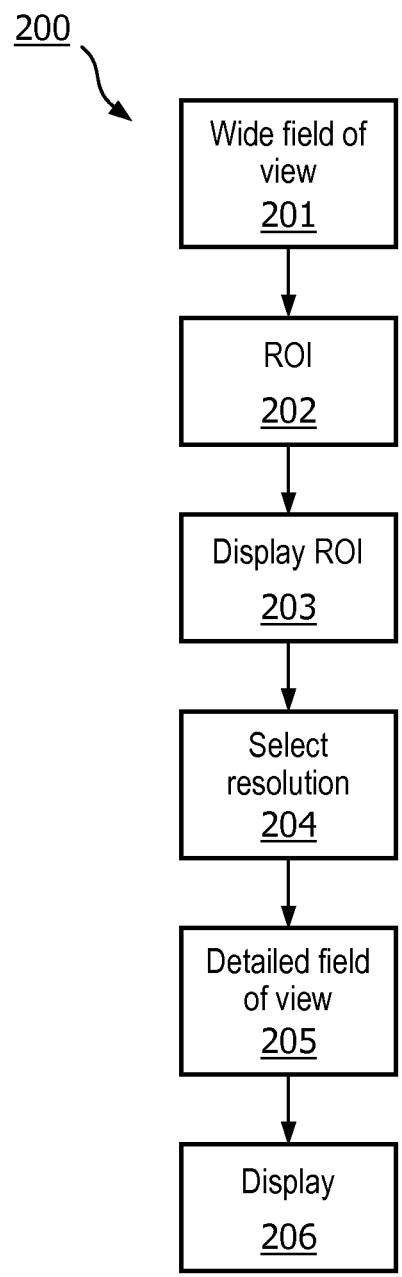
FIG. 14 illustrates a workflow for variable frequency image acquisition in accordance with the first embodiment of the present invention.

In FIG. 14 illustrates a workflow 200 for variable frequency image acquisition in accordance to the present invention. At step 201 the volumetric field of view 131 comprising the wide view 80 is imaged. In step 202 the ROI 82 is detected by the identifier, the automatic detection can be performed based on distinguishing anatomy feature 30, for example, or based on the user input. In step 203 outlines of the ROI may be displayed to the user. In addition, regions of the high intensity within the volumetric region are also identified and shown to the user. At this stage the user can also manually interact via the user interface 38 with the systems 100 adjusting the size, location of the ROI and the location of the high intensity regions. Further, in step 204 the user can select the desired resolution (or frequency) of the detail view of the ROI. The image processor 68 further translates the selected resolution into the transducer operation frequency. Alternatively, in this step the image processor 68 can compute an upper frequency limit, with which the ROI 82 can be imaged based on the fixed distance from the probe 10 (namely the transducer array 14 within the probe) to the ROI. The upper frequency limit can be also calculated based on several threshold frequency values: the first threshold value derived from the location of the high intensity region with respect to the steered angles of the beams within the ROI; and the second threshold frequency value an ultrasound wavelength being equal to the array pitch value. The In case the calculated upper frequency limit or the selected by user frequency is above the threshold value the beam steering parameters may be adjusted by the interferer analyzer 69. This information (the frequencies and steering angles) may be displayed on the display. In step 205 the system 100 would acquire the detail view of the ROI with increased resolution. In step 206 the wide and detailed fields of view are displayed to the user.

Figure 15:
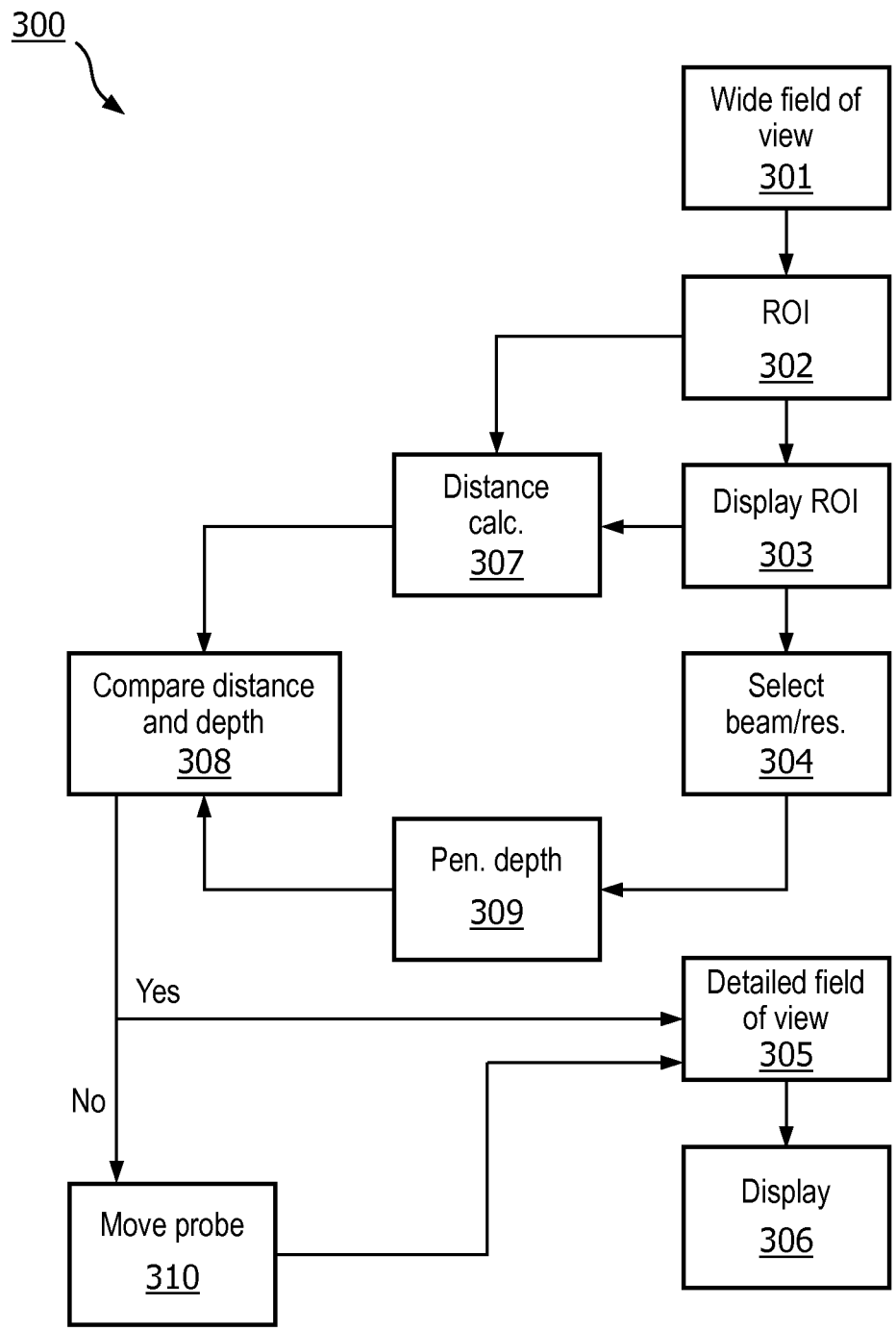
FIG. 15 illustrates a workflow for variable frequency image acquisition in accordance with the second embodiment of the present invention.

In FIG. 15 illustrates a workflow 300 for variable frequency image acquisition in accordance with another embodiment of the present invention. At step 301 the volumetric field of view 131 is acquired. In step 302 the ROI 82 is detected by the identifier. Regions of the high intensity within the volumetric region are also identified by the image processor. In step 303 outlines of the ROI and the locations of the high intensity regions may be displayed to the user. At this stage the user can also manually interact via the user interface 38 with the systems 100' adjusting the size, location of the ROI and the high intensity regions. In parallel, in step 307 the image processor 68 computes the distance from the probe to the most distant edge of RIO. Further, in step 304 the user can select the desired resolution (or frequency) of the detail view of the ROI. In this step the user may be given an indication of the optimal beam steering parameters for the selected resolution using a given ultrasound array. In step 309 based on this information the image processor 68 computes the penetration depth corresponding to the selected resolution (frequency). In step 308 the distance between the probe and the ROI is compared to the penetration depth. At this stage the interferer analyzer also adjusts the beam steering parameters if the high intensity region is detected. If the computed penetration depth is larger than the distance to the ROI, then the workflow is followed by step 305, in which the system 100 acquires the detail view of the ROI with the selected resolution and adjusted beam steering parameters. If the computed penetration depth is smaller than the distance to the ROI, then the workflow is followed by step 310, in which the drive mechanism provides probe's movement towards the ROI's location. A movement distance is determined by the ROI location, the selected resolution and beam steering parameters, wherein the parameters may be adjusted by the interferer analyzer depending on the presence of the high intensity region and the array's structural design. In case the movement distance is limited by an anatomy of the imaged volume (object), such that the probe cannot be moved further, the system 100' may provide a feedback to the user with a computed optimal resolution at which the ROI can be acquired taking into account anatomy limitations and the given array's pitch. Further, system 100 acquires the detail view of the ROI with the selected resolution or optimal suggested resolution in step 305. In step 306 the wide and detailed fields of view are displayed to the user.

It shall be understood by the person skilled in the art that the principles of the present invention can be practiced in both 2D and 3D ultrasound imaging.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound system for providing an ultrasound image of a volumetric region comprising a region of interest comprising:
   a probe having an array of CMUT transducers, wherein the array of CMUT transducers has a pitch value in at least one of azimuth dimension or elevation dimension, wherein the array of CMUT transducers is adapted to steer ultrasound beams in a variable frequency range over the volumetric region;
   a beamformer coupled to the array of CMUT transducers and adapted to control the ultrasound beam steering based on beam steering parameters and to provide an ultrasound image data of the volumetric region, wherein the ultrasound beams are steered using a steering angle within at least one of azimuth steering angle or elevation steering angle defined by the beam steering parameters;
   a transducer frequency controller coupled to the beamformer and adapted to vary operation frequencies of the array of CMUT transducers within the variable frequency range, wherein the transducer frequency controller is arranged to set the operation frequency to a first frequency for the ultrasound beams steered in the volumetric region and to change the operation frequency to a second frequency for the ultrasound beams steered within the region of interest, the second frequency being higher than the first frequency; and
   an image processor responsive to the ultrasound image data, wherein the image processor is adapted to identify a location of a high intensity region within the volumetric region, the high intensity region having signal intensity at least two times higher than the average intensity of the ultrasound image, wherein at least one of the beam steering parameters of the ultrasound beams steered within the region of interest is adjusted when the second frequency is above a first threshold frequency value derived from the location of the high intensity region with respect to the steering angle.

2. The ultrasound system according to claim 1, wherein the probe is an intracavity probe and the system further comprises:
   a drive coupled to the probe and the image processor, wherein the drive controls a movement of the probe with respect to the region of interest during imaging.

3. The ultrasound system according to claim 1, wherein the beam steering parameters comprise at least one of: ultrasound frequency, received signal spectrum filtration, the azimuth elevation steering angle or the elevation steering angle.

4. The ultrasound system according to claim 3, wherein the the beam steering parameters of the ultrasound beams steered within the region of interest is adapted based on the second frequency being reduced below the first threshold frequency value.

5. The ultrasound system according to claim 4, wherein the second frequency is reduced further below a second threshold frequency value, wherein the second frequency value is lower than the first threshold frequency value, wherein the second threshold frequency value corresponds to a transducer frequency for which an ultrasound wavelength is equal to the array pitch value.

6. The ultrasound system according to claim 4, wherein the second frequency is reduced further below a second threshold frequency value, wherein the second frequency value is lower than the first threshold frequency value, wherein the second threshold frequency value corresponds to a transducer frequency for which an ultrasound wavelength is equal to the array pitch value multiplied by two.

7. The ultrasound system according to claim 3, further comprising a user interface coupled to the image processor and responsive to a user manual selection of the region of interest and the high intensity region within the volumetric region, wherein the user interface is further enabled to adjust at least one of the beam steering parameters based on the user manual selection.

8. The ultrasound system according to claim 7, wherein the user manual selection further comprises:
   a frequency selection of the second frequency and the first frequency from the variable frequency range; and
   a beam steering parameter selection.

9. The ultrasound system according to claim 1, further comprising a user interface coupled to the image processor and responsive to a manual selection of the region of interest within the volumetric region, wherein the user interface is further enabled to adjust at least one of the beam steering parameters based on the user manual selection.

10. The ultrasound system according to claim 9, wherein the user interface is further responsive to a manual selection of the high intensity region within the volumetric region.

11. The ultrasound system according to claim 10, wherein the user manual selection comprises:
    a frequency selection of the second frequency and the first frequency from the variable frequency range; and
    a beam steering parameter selection.

12. The ultrasound system according to claim 9, wherein the at least one of the beam steering parameters of the ultrasound beams steered within the region of interest is adapted based on at least one of the azimuth steering angle or the elevation steering angle of the ultrasound beams steered within the region of interest is reduced.

13. A method of providing ultrasound images at variable frequencies of a volumetric region comprising a region of interest, wherein the method comprises:
    steering, using a steering angle, ultrasound beams in at least one of azimuth steering angle or elevation steering angle in a variable frequency range over the volumetric region, wherein the steering is performed based on beam steering parameters and by using an array of CMUT transducers, wherein the array of CMUT transducers has a pitch value in at least one of azimuth dimension or elevation dimension;

controlling the ultrasound beam steering and providing an ultrasound image data of the volumetric region, wherein the controlling comprises setting a frequency of the ultrasound beams steered within the volumetric region to a first frequency and changing the frequency to a second frequency for the ultrasound beams steered within the region of interest;

processing the ultrasound image data in order to produce an ultrasound image;

identifying a location of a high intensity region within the volumetric region, wherein a signal intensity of the region of high intensity is at least two times higher than the average intensity of the ultrasound image;

deriving a first threshold frequency value from the location of the high intensity region with respect to the steering angle; and adjusting at least one of the beam steering parameters of the ultrasound beams steered within the region of interest when the second frequency is above the first threshold frequency value.

14. The method according to claim 13 further comprising:

deriving a second threshold frequency value from an ultrasound wavelength being equal to the array pitch value; and further adjusting the beam steering parameters when the second frequency is above the second threshold frequency value.

* * * * *